United States Patent [19]

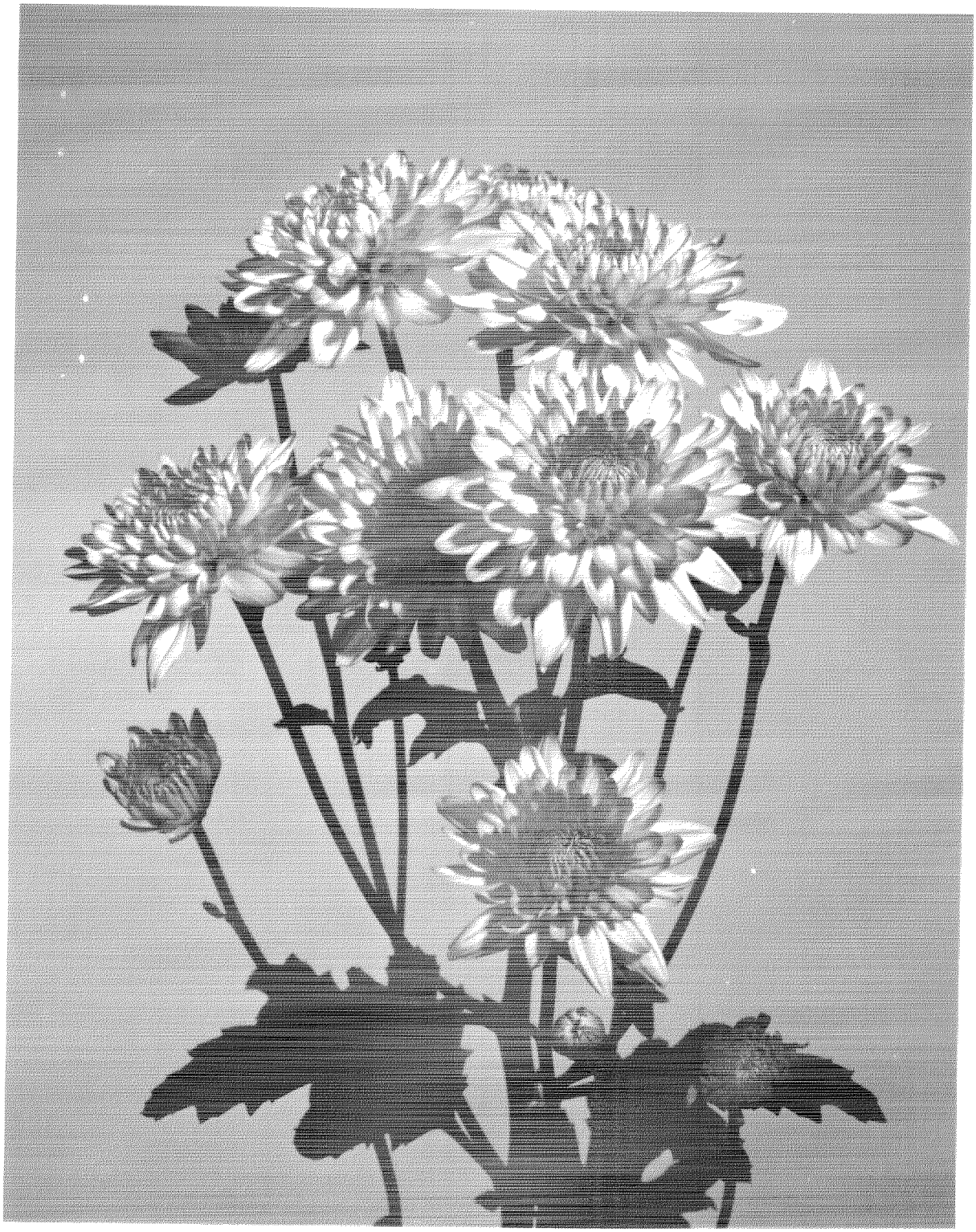

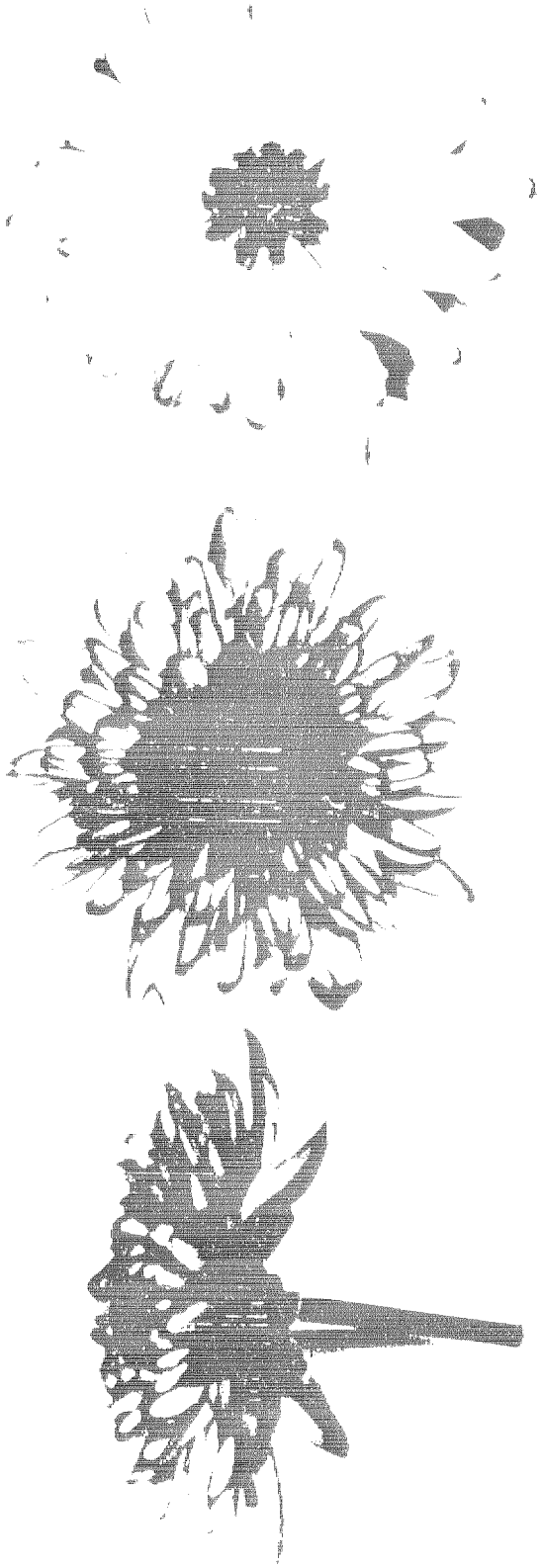

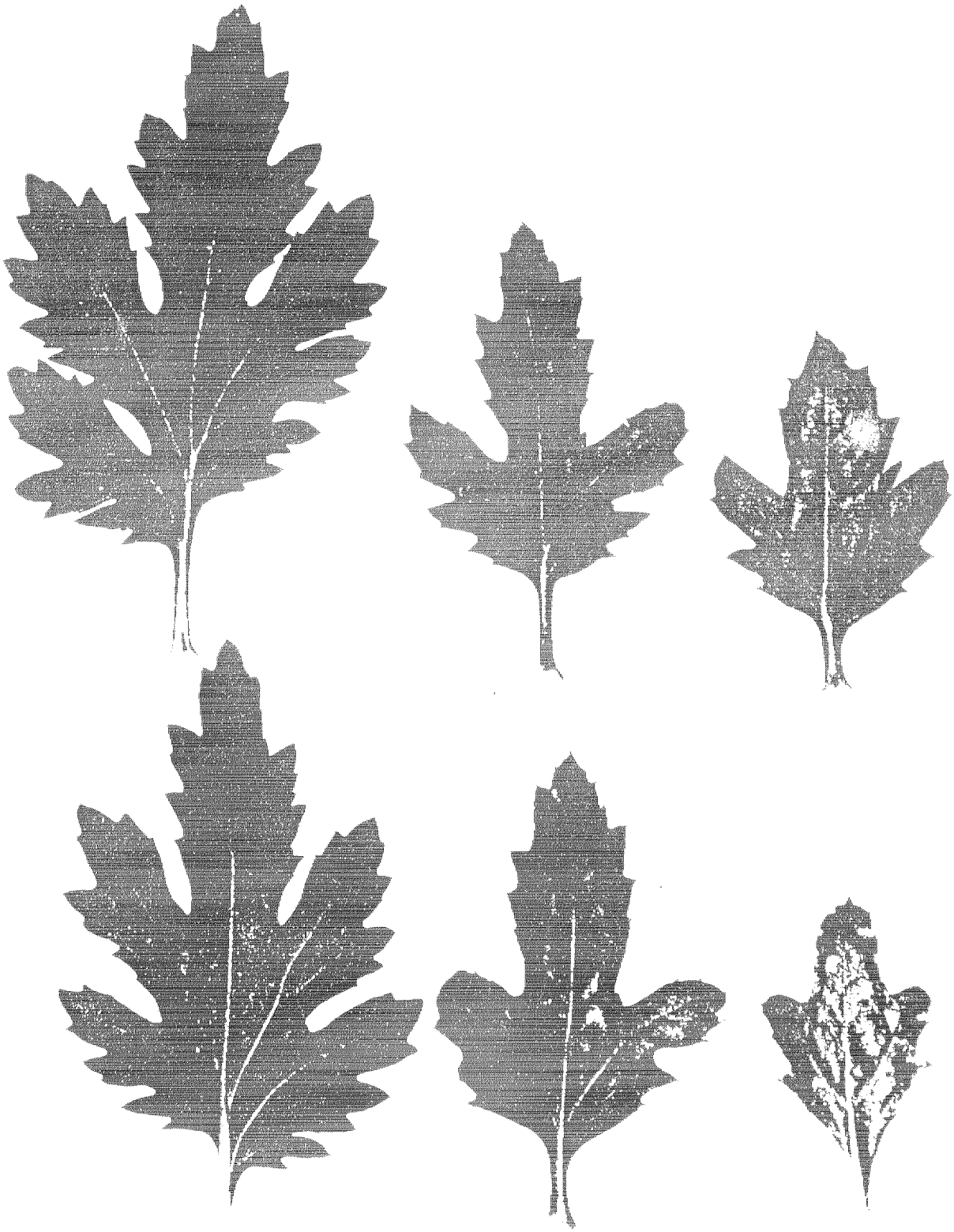

VandenBerg

[11] Patent Number: Plant 7,487

[45] Date of Patent: Apr. 2, 1991

[54] CHRYSANTHEMUM PLANT NAMED TOPACIO

[75] Inventor: Cornelis P. VandenBerg, Salinas, Calif.

[73] Assignee: Yoder Brothers, Inc., Barberton, Ohio

[21] Appl. No.: 481,102

[22] Filed: Feb. 26, 1990

[51] Int. Cl.[5] ..... A01H 5/00

[52] U.S. Cl. ..... Plt./76

[58] Field of Search ..... Plt./76, 80, 81, 82

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Topacio particularly characterized by its flat capitulum form; decorative capitulum type; purple ray floret color; diameter across face of capitulum of 75 to 89 mm when fully opened; flowering response in Salinas, Calif. under normal temperatures is 48 to 51 days after start of short days; flowering response in Bogota, Colombia under minimum 7 degrees Celsius night and maximum 29 degrees Celsius day is 66 to 70 days after start of short days; peduncle length of first lateral ranging from 7 to 15 cm, of the fourth lateral from 13 to 18 cm on open, terminal sprays; plant height of 89 to 99 cm when grown as a single stem cut mum in Salinas with 6 to 8 long days prior to start of short days compared to a height of 107 to 114 cm when grown in Bogota with 14 to 15 long days prior to start of short days; and excellent tolerance to low temperatures for bud initiation and flower development.

3 Drawing Sheets

The present invention comprises a new and distinct cultivar of Chrysanthemum, botalically known as *Dendranthema grandiflora,* and referred to by the cultivar name Topacio.

Topacio, identified as 85-239004, was originated from a cross made by Cornelis P. VandenBerg, in a controlled breeding program in Salinas, Calif., in 1984.

The female parent of Topacio was an unnamed seedling identified as 79-C06002, a pink decorative cut spray mum. The male parent of Topacio was also an unnamed seedling identified as 79-J14014, a bronze decorative cut spray mum with a high number of disc florets.

Topacio was discovered and selected as one flowering plant within the progeny of the stated cross by Cornelis P. VandenBerg in March 1986, in a controlled environment in Salinas, Calif.

The first act of asexual reproduction of Topacio was accomplished when vegetative cuttings were taken from the initial selection in May 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Topacio are firmly fixed and are related through successive generations of asexual reproduction.

Topacio has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsium night and 35 degrees Celsius day) flowering can be expected to be delayed and be more uneven than under normal temperatures. Normal temperatures can be described as 15 degrees Celsius minimum night and 25 degrees Celsius maximum day.

The following observations, measurements and comparisons describe plants grown in Salinas, Calif. and in Bogota, Colombia, under greenhouse conditions which approximate those generally used in commercial greenhouse practice. The low temperature tolerance was determined in repeated flowerings in Bogota, Colombia.

The following traits have been repeatedly observed and are determined to be basic characteristics of Topacio, which, in combination, distinguish this Chrysanthemum as a new and distinct cultivar:

1. Flat capitulum form.
2. Decorative capitulum type.
3. Purple ray floret color.
4. Diameter across face of capitulum of 75 to 89 mm when fully opened.
5. Flowering response in Salinas under normal temperatures is 48 to 51 days after start of short days. Flowering response in Bogota, Colombia under minimum 7 degrees Celsius night and maximum 29 degrees Celsius day is 66 to 70 days after start of short days.
6. Peduncle length of the first lateral at flowering after removing the apical bud without growth regulator applications is 10 to 15 cm when grown in Salinas, Calif., and 7 to 8 cm when grown in Bogota, Colombia. Peduncle length of the fourth lateral at flowering is 15 to 18 cm when grown in Salinas, and 13 to 15 cm when grown in Bogota.
7. Plant height is 89 to 99 cm when grown as a single stem cut mum in Salinas with 6 to 8 long days prior to start of short days, compared to a height of 107 to 114 cm when grown in Bogota with 14 to 15 long days prior to start of short days.
8. Excellent tolerance to low night temperatures for bud initiation and flower development. Average minimum low night temperatures in our Bogota trials ranged from 7 to 8.5 degrees Celsius.

The above measurements represent repeated flowerings over a period of a minimum of two years.

The accompanying photographic drawings show typical inflorescence and leaf characteristics of Topacio, with the colors being as nearly true as possible with illustrations of this type.

Sheet 1 is a color photograph of Topacio grown as a single step cut spray mum.

Sheet 2 is a black and white photograph of three views of the inflorescnece of Topacio.

Sheet 3 is a black and white photograph showing the upper and under sides of the leaves of Topacio at three stages of development (mature, intermediate and immature).

Of the commercial cultivars known to the inventor, the most similar in comparison to Topacio is the cultivar Gallant, a purple flat decorative cut spray mum disclosed in U.S. Plant Pat. No. 5,915. Reference is made to attached Chart A which compares certain characteristics of Topacio to the same characteristics of Gallant.

Similar traits are ray floret color, capitulum form and type, spray formation, and low temperature tolerance. The peduncle length of both cultivars is comparable. The flower size of Topacio is significantly smaller than that of Gallant, and the flower form is much more formal than the somewhat ragged flower form of Gallant. Topacio also has a shorter plant height and a faster flowering response in Salinas than Gallant. The flowering response in Bogota of both cultivars is comparable.

In the following description color references are made to The Royal Horticultural Society Colour Chart. The color values were determined on plant material grown in Salinas, Calif. on July 15, 1989.

Classification:

*Botanical.*—*Dendranthema grandiflora* cv Topacio.

*Commercial.*—Decorative cut spray mum.

INFLORESCENCE

A. Capitulum:

*Form.*—Flat.

*Type.*—Decorative.

*Diameter across face.*—75 to 89 mm when fully opened.

B. Corolla of ray florets:

*Color (general tonality from a distance of three meters).*—Purple.

*Color (upper surface).*—75A to 75B.

*Color (under surface).*—75D.

*Shape.*—Straight, oblong, slightly ribbed. The sides of the apical part of the petals tend to fold or bend down when mature.

C. Corolla of disc florets:

*Color (mature).*—Closest to 14A.

*Color (immature).*—Closest to 144B.

D. Reproductive organs:

*Androecium.*—Present on disc florets only; very few disc florets, barely visible in the mature flower; scant pollen.

*Gynoecium.*—Present on both ray and disc florets.

PLANT

A. General appearance:

*Height.*—Plant height is 89 to 99 cm when grown as a single stem cut mum in Salinas with 6 to 8 long days prior to start of short days; height is 107 to 114 cm when grown in Bogota with 14 to 15 long days prior to start of short days.

B. Foliage:

*Color (upper surface).*—147A.

*Color (under surface).*—147B.

*Shape.*—See photograph.

CHART A

COMPARISON OF TOPACIO AND GALLANT

| CHARACTERISTIC | TOPACIO | GALLANT |
|---|---|---|
| Ray floret color | Purple | Purple |
| Capitulum form | Flat | Flat |
| Capitulum type | Decorative | Decorative |
| Spray formation | Terminal | Terminal |
| Peduncle length: | | |
| 1st lateral, Salinas | 10 to 15 cm | 8 to 10 cm |
| 4th lateral, Salinas | 15 to 18 cm | 15 to 18 cm |
| 1st lateral, Bogota | 7 to 8 cm | 8 to 10 cm |
| 4th lateral, Bogota | 13 to 15 cm | 13 to 18 cm |
| Diameter across face of capitulum | 75 to 89 mm | 100 to 125 mm |
| Plant height: | | |
| 6-8 long days, Salinas | 89 to 99 cm | Not available |
| 14-15 long days, Bogota | 107 to 114 cm | 122 to 130 cm |
| Flowering response period: | | |
| in Salinas | 48 to 51 days | 53 to 62 days |
| in Bogota | 66 to 70 days | 63 to 70 days |
| Low night temperature tolerance | Excellent | Excellent |

COMPARISONS MADE OF PLANTS GROWN AS SINGLE STEM SPRAY CUT MUMS IN SALINAS, CALIFORNIA, AND IN BOGOTA, COLOMBIA

I claim:

1. A new and distinct Chrysanthemum plant named Topacio, as described and illustrated.

* * * * *